United States Patent [19]

Naito et al.

[11] Patent Number: 4,692,519
[45] Date of Patent: Sep. 8, 1987

[54] CRYSTALS OF SODIUM CEPHEMCARBOXYLATE

[75] Inventors: Kenzo Naito, Kyoto; Kazuo Tsukamura, Hyogo; Sakae Aoyagi, Saitama, all of Japan

[73] Assignees: Lederle (Japan), Ltd., Kyobashi; Takeda Chemical Industries, Ltd., Jusohonmachi, both of Japan

[21] Appl. No.: 674,745

[22] Filed: Nov. 26, 1984

[30] Foreign Application Priority Data

Dec. 2, 1983 [JP] Japan .................................. 58-228868

[51] Int. Cl.[4] .................. C07D 501/56; A61K 31/545
[52] U.S. Cl. ..................................................... 540/227
[58] Field of Search ........................... 544/27; 540/227

[56] References Cited

U.S. PATENT DOCUMENTS

| | | | |
|---|---|---|---|
| 4,104,470 | 8/1978 | Cise et al. | 544/20 |
| 4,224,371 | 9/1980 | Amiord et al. | 544/20 |
| 4,341,777 | 7/1982 | White | 514/207 |
| 4,399,132 | 8/1983 | Curran et al. | 540/227 X |
| 4,464,367 | 8/1984 | Labeeuw | 544/27 |

FOREIGN PATENT DOCUMENTS

| | | | |
|---|---|---|---|
| 60028 | 9/1982 | European Pat. Off. | 544/24 |
| 94632 | 11/1983 | European Pat. Off. | 544/26 |

OTHER PUBLICATIONS

Kodama et al., ". . . Crystal Structure of a Semi-Synthetic Cephalosporim . . . ", *Chem. Abst.* 101:191445k (1983).

The Journal of Antibiotics, vol. 36, No. 2, pp. 179 and 180 (1983).

*Primary Examiner*—Donald G. Daus
*Assistant Examiner*—William A. Teoli, Jr.
*Attorney, Agent, or Firm*—Wegner & Bretschneider

[57] ABSTRACT

Novel crystals of sodium 7β-[2-(2-aminothiazol-4-yl)-(Z)-2-methoxyiminoacetamido]-3-[(1,2,3-thiadiazol-5-yl)thiomethyl] ceph-3-em-4-carboxylate showing characteristic peaks at interplanar spacings (d) of 9.3, 8.9, 5.3, 5.1, 4.4, 4.3 and 3.8 Å in the powder X-ray diffraction pattern which are very stable and do not easily cause discoloration and decomposition.

1 Claim, No Drawings

CRYSTALS OF SODIUM CEPHEMCARBOXYLATE

This invention relates to crystals of sodium 7β-[2-(2-aminothiazol-4-yl)-(Z)-2-methoxyiminoacetamido]-3-[(1,2,3-thiadiazol-5-yl)thiomethyl]ceph-3-em-4-carboxylate and to a method for producing the same.

7β-[2-(2-Aminothiazol-4-yl)-(Z)-2-methoxyiminoacetamido]-3-[(1,2,3-thidiazol-5-yl)thiomethyl]ceph-3-em-4-carboxylic acid (hereinafter referred to as "MTC") is an interesting cephemcarboxylic acid, represented by the formula:

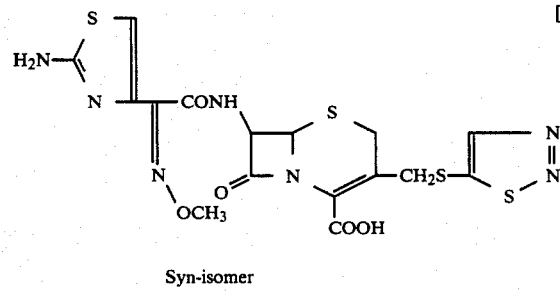

Syn-isomer which exhibits potent antimicrobial activity against both gram-positive and gram-negative bacteria (Curran et al. U.S. Pat. No. 4,399,132).

However, the sodium salt of this cephemcarboxylic acid, which is the most advantageous for the preparation of injectable solutions, has heretofore been produced only in the amorphous forms, and there have been encountered the problems that such an amorphous solid, with its inadequate stability, undergoes discoloration and fails to retain its chemical integrity and potency when stored under ordinary conditions for a prolonged period of time. Moreover, it requires the industrially unfavourable purification steps such as column chromatography to produce this amorphous solid in the substantially pure form, and this has constituted another problem.

In view of the above, the present inventors carried out intensive investigation in order to solve these problems, and as a result, found that sodium 7β-[2-(2-aminothiazol-4-yl)-(Z)-2-methoxyiminoacetamido]-3-[(1,2,3,-thiadiazol-5-yl)thiomethyl]ceph-3-em-4-carboxylate (hereinafter referred to as "MCT.Na") can be obtained in the form of stable crystals and can also be purified easily through crystallization. These findings were followed by further investigation, which has culminated in the present invention.

Thus, the present invention is directed toward crystals of MTC.Na which show their characteristic peaks at interplanar spacings (d) of 9.3, 8.9, 5.3, 5.1, 4.4, 4.3 and 3.8 Å in the powder X-ray diffraction pattern.

The crystals of MTC.Na provided by the present invention are demonstrated to have a crystal form by observation under a polarization microscope and powder X-ray diffraction analysis, and show their characteristic peaks at the above-mentioned interplanar spacings (d) in the powder X-ray diffraction pattern.

Referring now to a method for producing the crystals of the present invention, as a starting material, there is used a liquid containing MTC.Na and water. This liquid desirably has a ratio of MTC.Na to water in the range of ⅓ to 10 parts by weight of the latter against 1 part by weight of the former. For the purpose of preparing this liquid, there may be adopted various methods; for example, the amorphous solid of MTC.Na may be dissolved in water to make a solution of concentration in the range of about 10 to about 70 weight %; the MTC is neutralized with alkali whose cation is Na⁺ (e.g., NaOH, Na₂CO₃, NaHCO₃) in water, alternatively, a dilute aqueous solution of MTC.Na is treated with an adsorbent such as activated carbon, if desired, followed by concentration; or the amorphous solid of MTC.Na is allowed to absorb the moisture and to undergo deliquescence.

This liquid may also contain hydrophilic solvents, such as ethanol, n- or iso-propanol and acetone. With reference to their content, too large quantities are not preferred, and in the case of ethanol, not more than 2 to 3 parts by volume of ethanol for 1 part by weight of water is preferable. In addition, this liquid may be contaminated with some amounts of the impurities inherent to the production steps.

In order to allow the crystals of MTC.Na to crystallize out of this liquid, this liquid is maintained at a temperature of about 0° C. to about 40° C., preferably about 3° C. to 30° C., for a period of time long enough to allow the crystals of the present invention to separate out. When the crystals are allowed to crystallize out of a liquid of high concentration, it is desirable to carry out such a procedure under a highly humid atmosphere with relative humidity in the range of 80 to 100%.

Crystallization of the crystals in some instances requires a fairly long period of time, depending upon the content of impurities, the concentration of the liquid, etc., but seeding with the crystals of MTC.Na obtained by the method of the present invention can reduce the time to within several hours. It is also possible to increase the crystallization amount of the crystals of MTC.Na by allowing neutral salts containing Na⁺, such as NaCl, Na₂SO₄, NaBr and Na₂HPO₄, to coexist in the liquid.

The crystals which have been allowed to crystallize out by the above procedure, can be dried as such in accordance with the conventional method to produce the crystals of the present invention, only when water is used alone as a crystallizing solvent and the substantial purity of the compound of the formula [I] being used as a starting material is of the desired degree of purity. In the crystallization procedure according to the present invention, however, undesirable impurities migrate into the mother liquor, thus permitting effective purification, and therefore, filtration of a mixture containing the crystals, followed by washing with a mixed solution of water and organic solvent, can permit removal from the crystals of the residual mother liquor containing the undesirable impurities. As such an organic solvent, there may be mentioned, for example, ethanol, n- or iso-propanol, n- or iso-butanol and acetone. Among them, ethanol is the most preferable, and frequent use is made of the method which comprises washing the crystals which have separated out with a cold mixed solution of water and ethanol (e.g., 1:2 to 4, on a volume basis).

The crystals as washed in the above-mentioned manner contain the organic solvent adhering thereto, and in order to remove it, it is recommendable to contact the crystals with water vapor at a temperature of about 10° C. to about 40° C. for a sufficient length of time. This procedure is carried out, for example, by allowing moist air or moist nitrogen gas with relative humidity of not less than about 70% to coexist with the crystals containing solvent adhering, alternatively passing these moist gas streams through the crystals placed in layers or placing the crystals within a system maintaining water vaporizing under reduced pressure. This procedure can also be conducted after drying in advance the washed crystals by the conventional method to remove the major portion of the solvent.

The organic solvent which has adhered to the crystals is difficult to remove under usual drying conditions. For example, ethanol when used for washing remains adhering in a small amount at a ratio in the neighborhbod of about 1%, but can be removed by the above-mentioned procedure.

The crystals having the organic solvent thus removed are then subjected to drying according to the conventional method. The crystals, under conditions of relative humidity of 75 to 95% and temperature of about 25° C., tend to reach the equilibrium moisture of about 9%, and can be dried easily to a moistute content of about 3%. Their moisture content can be further reduced, depending upon the drying conditions employed. When considering the stability of the resulting finished crystals, it is preferable to dry the crystals to a moisture content of not more than 8%.

The crystals according to the present invention are far more stable as compared with the amorphous solids of MTC.Na produced conventionally by the prior art, and are advantageous in terms of storage and transportation.

Furthermore, these crystals are substantially pure, and can be prepared, together with pharmacologically acceptable carriers if desired, into pharmaceutical formulations containing the said crystals as an active ingredient.

The compound of the formula [I], which is the starting material of the present invention, can be produced, for example, by the method as described in Curran et al. U.S. Pat. No. 4,399,132 or by methods equivalent thereto, and the compounds produced by these methods can be used, after being purified or without being purified, as the starting material of the present invention.

The invention is illustrated by the following non-limiting examples:

EXAMPLE 1

To 143 mg of MTC.Na in the form of a lyophilized product (with a moisture content of 2.6% and an MTC.Na content of 97%, which product was demonstrated to be amorphous by powder X-ray diffraction analysis) was added 65 mg of water to dissolve the compound, and the solution was allowed to stand under an atmosphere of 20° to 25° C. with relative humidity of 90 to 100% for 15 hours. As crystals separated out, the solution turned into a paste-like material. This paste-like material was left standing under an atmosphere of about 25° C. with relative humidity of about 75% for 3 days, and the resulting solid product was pulverized to give 125 mg of crystals of MTC.Na as a yellowish white powder.

Elemental analysis: Found: C, 32.55 H, 3.37; N, 16.71; S, 22.05 Calcd. ($C_{16}H_{14}N_7O_5S_4Na.3H_2O$) C, 32.59; H, 3.42; N, 16.63; S, 21.75

Powder X-ray diffraction pattern (with $CuK\alpha$ used as a radiation source):

Characteristic peaks shown at interplanar spacings (d) of 9.3, 8.9, 5.3, 5.1, 4.4, 4.3 and 3.8 Å.

EXAMPLE 2

In 0.100 ml of water was dissolved 0.238 g of an amorphous powder (with a moisture content of 3.0% and an MTC.Na content of 93%). About 5 mg of seed crystals were added to the yellowish brown solution, followed by stirring at 25° to 30° C. for 40 minutes to allow crystals to separate out, and a mixed solution consisting of 0.5 ml of water and 4.6 ml of n-propanol was added to the mixture, followed by stirring at 20° to 25° C. for about 15 hours. The crystals which separated out were recovered by filtration, washed with a mixed solution (1:8) of water and n-propanol and dried under reduced pressure of 20 to 30 mmHg at 20° to 25° C. for 1.0 hour. The crystals were allowed to stand in a vessel containing water separately existing therein at 20° to 25° C. for 15 hours, and then dried under reduced pressure of 10 to 20 mmHg at 20° to 25° C. to give 0.171 g of crystals of MTC.Na as a yeollowish white powder.

Elemental analysis: Found: C, 33.58; H, 3.22; N, 17.10; S, 22.50 Calcd. ($C_{16}H_{14}N_7O_5S_4.2H_2O$) C, 33.62; H, 3.17; N, 17.15; S, 22.44

H-NMR ($D_2O$): 3.58 (2H, AB quartet, J=18 Hz, 2-$CH_2$), 3.99 (3H, singlet, —$OCH_3$), 4.15 (2H, AB quartet, J=14 Hz, 3$CH_2$), 5.18 (1H, doublet, J=5 Hz, $C_6$-H), 5.77 (1H, doublet, J=5 Hz, $C_7$-H), 7.00 (1H, singlet, thiazole ring-H), 8.70 (1H, singlet, thiadiazole ring-H)$\delta$ ppm.

IR (KBr): 1760, 1670, 1605, 1530 $cm^{-1}$

Powder X-ray diffraction pattern: The same characteristic peaks as obtained in Example 1 were shown. n-Propanol content (measured by gas chromatography): Not more than 0.1%.

EXAMPLE 3

(1) In a mixed solution consisting of 10 ml of water and 10 ml of ethanol was dissolved 10.5 g of an amorphous powder (with a water content of 2.7% and an MTC.Na content of 91%) of MTC.Na, and 10 ml of ethanol was added dropwise to the solution at 17° to 20° C. under gradual stirring, followed by stirring at the same temrperature for 2 hours. The crystals which separated out were filtered by a glass filter and washed with 2.0 ml of an ice-cooled mixed solution (1:2) of water and ethanol. A nitrogen gas humidified by the passage through water at 20° C. was passed through the crystal layer in the glass filter at a flow rate of about 4 l/min for 4 hours, followed by passing a dry nitrogen gas at the same flow rate for 1 hour to give 9.3 g of crystals of MTC.Na as a yellowish white powder.

Powder X-ray diffraction pattern: The same characteristic peaks as obtained in Example 1 were shown.

Moisture content (Karl Fischer's method): 7.9%

Ethanol content: (measured by gas chromatography): Not more than 0.1%.

(2) A 3.0 g portion of the crystals as obtained in (1) was dried under reduced pressure of about 20 mmHg at about 20° C. for 1.0 hour to give crystals with a moisture content of 7.4%. A 2.0 g portion of the crystals was further dried under reduced pressure of about 20 mmHg at about 40° C. for 2 hours to give crystals with a moisture content of 5.0%. A 1.0 g portion of the crystals was further dried under reduced pressure of about 1 mmHg at about 40° C. for 2.0 hours to give crystals with a moisture content of 1.3%. The resultant crystals with a moisture content of 1.3% showed the same characteristic peaks in the powder X-ray diffraction pattern as those obtained in Example 1.

EXAMPLE 4

In a mixed solution consisting of 120 ml of water and 60 ml of ethanol was dissolved 122 g of an amorphous powder (with a moisture content of 2.7% and an MCT.Na content of 91%) of MTC.Na, and after about 0.1 g of seed crystals was added, 60 ml of ethanol was added to the solution at 20° to 25° C. over the period of 3 hours with gradual stirring, whereupon crystals were allowed to separate out and then to undergo aging for 30 minutes. The crystals were recovered by filtration, washed with three 40 ml portions of an ice-cooled mixed soltuion (1:1) of water and ethanol and then with two 40 ml portions of a mixed solution (1:8) of water and ethanol, allowed to stand in a tightly closed vessel containing water separately existing therein at 20° to 25° C. for 2 days to remove the ethanol from the crystals, and dried under reduced pressure of about 20 mmHg at 20° to 25° C. for 10 hours to give 91.2 g of crystals of MTC.Na as a yellowish white powder.

Powder X-ray diffraction pattern: The same characteristic peaks as obtained in Example 1 were shown.

Moisture content (Karl Fischer's method): 7.8%

Ethanol content (measured by gas chromatography): Not more than 0.1%.

EXAMPLE 5

(1) In 1.0 ml of a mixed solution (1:1) of water and ethanol was dissolved 0.50 g of an amorphous powder (with a moisture content of 3.0% and an MTC.Na content of 93%) of MTC.Na, and 0.75 ml of ethanol was added dropwise to the solution at 10° to 15° C. with stirring, followed by stirring for 10 minutes. The solution was allowed to stand for 1.5 hours, and the crystals which separated out were recovered by filtration. The crystals were washed with 0.5 ml of an ice-cooled mixed solution (1:2.5) of water and ethanol and dried under reduced pressure of 10 to 20 mmHg at about 20° C. for 6 hours to give 0.41 g of crystals of MTC.Na as a yellowish white powder.

Powder X-ray diffraction pattern: The same characteristic peaks as obtained in Example 1 were shown.

Moisture content (Karl Fischer's method): 5.1%

Ethanol content (measured by gas chromatography): 1.3%.

(2) A 0.20 g portion of the crystals as obtained in (1) was dried under reduced pressure of about 1 mmHg at about 40° C. for 5 hours to give crystals with a moisture content of 1.3% and an ethanol content of 1.3%.

(3) A 0.1 g portion of the crystals as obtained in (1) was allowed to stand in a tightly closed vessel containing water separately existing therein for 18 hours, and then dried under reduced pressure of 10 to 30 mmHg at about 20° C. for 2 hours to give crystals with an ethanol content of not more than 0.1%.

EXAMPLE 6

In 6.0 ml of water was dissolved 1.0 g of an amorphous powder (with a moisture content of 3.0% and an MTC.Na content of 93%) of MTC.Na, and 0.6 g of sodium chloride was added little by little to the solution at 20° to 25° C. over the period of 3 hours with stirring. The crystals which separated out were recovered by filtration, washed with 1.5 ml of a 1% aqueous sodium chloride solution and allowed to stand for drying in an atmosphere of temperature of about 25° C. and relative humidity of about 75% for 2 days to give 0.65 g of crystals of MTC.Na.

Powder X-ray diffraction pattern: The same characteristic peaks as obtained in Example 1 were shown.

Moisture content (Karl Fischer's method): 9.0%.

EXPERIMENT EXAMPLE

The crystalline powder of MTC.Na as prepared by the method of the present invention and the amorphous powder of MTC.Na as prepared according to the prior art (the method described in Curran et al. U.S. Pat. No. 4,399,132, Example 3) were each stored in a dark place in the respective, tightly closed vessels at different temperatures of room temperature, 40° C. and 50° C., respectively, and inspected for appearance (color) and percentage of potency retained, 3 and 6 months later, respectively, with the results being shown as follows.

| Storage conditions | Forms of powder | | | |
| --- | --- | --- | --- | --- |
| | Crystalline powder. A moisture content of 7.4% | Crystalline powder A moisture content of 5.9% | Crystalline powder A moisture content of 1.4% | Amorphous powder A moisture content of 2.7% |
| At the start of storage | Yellowish white 100% | Yellowish white 100% | Yellowish white 100% | Yellowish white 100% |
| 3 Months later: | | | | |
| Room temp. | Yellowish white 100% | Yellowish white 100% | Yellowish white 100% | Yellow white 95% |
| 40° C. | Yellowish white 100% | Yellowish white 100% | Yellowish white 100% | Brownish 85% |
| 50° C. | Yellow white 100% | Yellow white 100% | Yellow white 97% | Brown — |
| 6 Months later: | | | | |
| Room temp. | Yellowish white 100% | Yellowish white 100% | Yellowish white 100% | Light orange 93% |
| 40° C. | Yellow white 100% | Yellow white 100% | Yellow white 99% | Brown 79% |
| 50° C. | Yellow white 100% | Yellow white 100% | Yellow white 97% | — |

(Note: the upper row in each column indicates the color of the powder, with the lower row showing the percentage of potency retained.)

What is claimed is:

1. Crystals of sodium 7β-[2-(2-aminothiazol-4-yl)-(Z)-2-methoxyiminoacetamido]-3-[(1,2,3-thiadiazol-5-yl)thiomethyl]ceph-3-em-4-carboxylate showing their characteristic peaks at interplanar spacings (d) of 9.3, 8.9, 5.3, 5.1, 4.4, 4.3, and 3.89 Å in the powder X-ray diffraction pattern.

* * * * *